United States Patent [19]
Aotsuka et al.

[11] Patent Number: 5,543,420
[45] Date of Patent: Aug. 6, 1996

[54] QUINOLINE-3-ACETIC ACID DERIVATIVE, PROCESS FOR PRODUCTION THEREOF AND USE THEREOF

[75] Inventors: Tomoji Aotsuka, Hamura; Toshiyuki Nishio, Kawasaki; Hiroshi Hosono, Ibaraki; Yoshiyuki Nakamura, Shizuoka; Tetsuo Matsui, Tsukuba; Hiromichi Ishikawa, Kobe, all of Japan

[73] Assignees: The Green Cross Corporation; Senju Pharmaceutical Co., Ltd., both of Osaka, Japan

[21] Appl. No.: 295,876

[22] PCT Filed: Jan. 6, 1994

[86] PCT No.: PCT/JP94/00007

§ 371 Date: Nov. 10, 1994

§ 102(e) Date: Nov. 10, 1994

[87] PCT Pub. No.: WO94/15934

PCT Pub. Date: Jul. 21, 1994

[30] Foreign Application Priority Data

Jan. 6, 1993 [JP] Japan ..................... 5-15899

[51] Int. Cl.$^6$ .................. C07D 417/06; C07D 215/227; A61K 31/47; A61K 31/425
[52] U.S. Cl. ......................... 514/312; 546/157; 546/158
[58] Field of Search ................... 546/157, 158; 514/312

[56] References Cited

U.S. PATENT DOCUMENTS

| | | | |
|---|---|---|---|
| 5,143,930 | 9/1992 | Yoshioka | 514/369 |
| 5,258,382 | 11/1993 | Negoro | 514/249 |
| 5,262,433 | 11/1993 | Horio | 514/381 |

OTHER PUBLICATIONS

Elgemeie, "Nitriles in Heterocyclic Synthesis . . .", *Heterocycles*, vol. 24, No. 2, pp. 349–353, 1986.
Fathy, "Nitriles in Heterocylic Synthesis . . .", *Arch Pharm (Weinhiem)*, vol. 321, pp. 509–512, 1988.

*Primary Examiner*—C. Warren Ivy
*Assistant Examiner*—D. Margaret M. Mach
*Attorney, Agent, or Firm*—Sughrue, Mion, Zinn, Macpeak & Seas

[57] ABSTRACT

A quinoline-3-acetic acid derivative of the formula

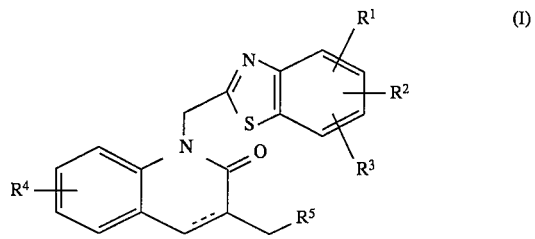

(I)

wherein $R^1$, $R^2$ and $R^3$ are the same or different and each is a hydrogen atom or a halogen atom, $R^4$ is a hydrogen atom, a halogen atom or a substituted or unsubstituted lower alkyl, $R^5$ is an optionally esterified carboxyl and the broken line means an optional presence of a double bond, and a pharmaceutically acceptable salt thereof. The novel compound of the formula (I) and a pharmaceutically acceptable salt thereof of the present invention have an aldose reductase inhibitory activity in mammals inclusive of human and are highly safe. Accordingly, they are useful as pharmaceutical compositions for the treatment of the complications of diabetes, such as faulty union of corneal injury, cataract, neurosis, retinopathy and nephropathy, particularly cataract and neurosis.

13 Claims, No Drawings

QUINOLINE-3-ACETIC ACID DERIVATIVE, PROCESS FOR PRODUCTION THEREOF AND USE THEREOF

This application is a 371 of PCT/JP94/00007, filed 6 Jan. 1996.

TECHNICAL FIELD

The present invention relates to a novel quinoline-3-acetic acid derivative having a superior aldose reductase inhibitory activity, a pharmaceutically acceptable salt thereof, a process for the production thereof and a pharmaceutical agent containing said compound.

The compounds of the present invention mentioned above (which include the above-mentioned derivative and a pharmaceutically acceptable salt thereof, hereinafter the same) are useful as aldose reductase inhibitors and for the prevention and/or treatment of the complications of diabetes, such as faulty union of corneal injury, diabetic cataract, retinopathy, nephropathy and neurosis.

BACKGROUND ART

For treating diabetes, blood sugar regulators such as insulin and synthetic hypoglycemic agents have been conventionally used widely. Diabetes is a disease which accompanies various complications which are hardly prevented from developing by a mere control of the blood sugar, and a new therapeutic agent for the complications of diabetes has been demanded. Accumulation of and increase in sorbitol and galactitol in tissues which are caused by chronic hyperglycemia have recently been drawing attention as the mechanism of the onset of the complications of diabetes.

Some literatures suggest that a compound having an inhibitory action on the activity of aldose reductase, which is an enzyme capable of converting aldose such as glucose or galactose into sorbitol or galactitol, is useful for the treatment of the complications of diabetes, such as faulty union of corneal injury, cataract, neurosis, nephropathy and retinopathy [see J. H. Kinoshita et al., Biochem. Biophys, Acta, 158, 472 (1968), Richard Poulson et al. Biochem. Pharmacol., 2, 1495 (1983) and D. Dvornik et al., Science, 182, 1145 (1973)].

Based on the foregoing, the study is directed to the prevention and treatment of the complications of diabetes by the inhibition of aldose reductase activity to ultimately inhibit accumulation of polyols such as sorbitol and galactitol.

Of the compounds synthesized for this end, various 1,4-benzothiazine- 4-acetic acid derivatives have aldose reductase inhibitory action as reported in Japanese Patent Unexamined Publication Nos. 40264/1986 and 107970/1988. Yet, the development of a therapeutic agent for the complications of diabetes, which has a still more excellent aldose reductase inhibitory action, is desired.

DISCLOSURE OF THE INVENTION

In view of the above, the present inventors have conducted intensive studies with the aim of developing a therapeutic agent for the complications of diabetes, which has an aldose reductase inhibitory action, and found that a certain quinoline derivative can achieve the object, which resulted in the completion of the invention.

That is, the present invention provides a quinoline-3-acetic acid derivative of the formula (I)

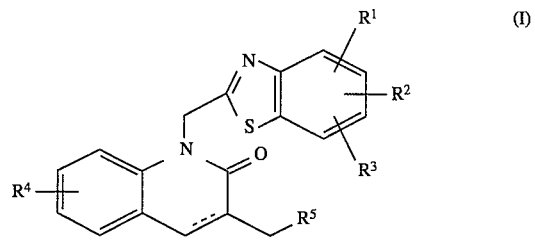

wherein $R^1$, $R^2$ and $R^3$ are the same or different and each is a hydrogen atom or a halogen atom, $R^4$ is a hydrogen atom, a halogen atom or a substituted or unsubstituted lower alkyl, $R^5$ is an optionally esterified carboxyl and the broken line means an optional presence of a double bond, or a pharmaceutically acceptable salt thereof; a process for producing the aforementioned quinoline-3-acetic acid derivative or a pharmaceutically acceptable salt thereof, comprising reacting a compound of the formula (II)

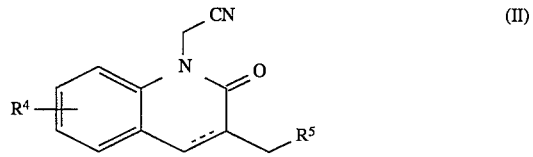

wherein $R^4$, $R^5$ and the broken line are as defined above, or a salt thereof with a compound of the formula (III)

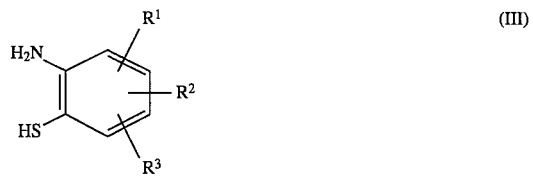

wherein $R^1$, $R^2$ and $R^3$ are as defined above, or an acid addition salt thereof and hydrolysis where necessary; and a composition containing the compound as an active ingredient.

The compound of the formula (I) of the present invention has a novel structure essentially comprising a quinoline-3-acetic acid moiety as the basic structure.

Examples of the halogen atom include fluorine atom, chlorine atom, bromine atom and iodine atom. The substituted or unsubstituted lower alkyl is preferably a straight or branched alkyl having 1 to 6 carbon atoms such as methyl, ethyl, propyl, isopropyl, butyl, isobutyl, sec-butyl, tert-butyl, pentyl, isopentyl, sec-pentyl, tert-pentyl, hexyl, isohexyl, sec-hexyl and tert-hexyl. These lower alkyl groups may be substituted by aryl, amino, halogen atom (exemplified by those mentioned above), cyano, hydroxy or the like.

Examples of the optionally esterified carboxyl include carboxyl, alkoxycarbonyls such as methoxycarbonyl, ethoxycarbonyl, propoxycarbonyl, isopropoxycarbonyl, butoxycarbonyl, isobutoxycarbonyl, tert-butoxycarbonyl, cyclohexyloxycarbonyl and cyclopentyloxycarbonyl, aryloxycarbonyl optionally having substituents on the benzene ring, such as halogen atom (exemplified by those mentioned above), alkyl, alkoxyl and nitro, and benzyloxycarbonyl.

$R^1$, $R^2$ and $R^3$ may be bonded at either of the 4th–7th positions of benzothiazole group. The two of these are preferably bonded at 4- and 5-positions, 5- and 7-positions or 6- and 7-positions and $R^1$, $R^2$ and $R^3$ are preferably bonded at 4-, 5- and 7-positions. It is also preferable that $R^1$, $R^2$ and $R^3$ should be halogen atoms at the same time and it is most preferable that all of them are fluorine atoms, bromine atoms or chlorine atoms.

While $R^4$ may take the optional position from 5th to 8th positions, it is preferably bonded at the 6-position. $R^4$ is preferably hydrogen atom, lower alkyl or halogen atom and most preferably hydrogen atom, methyl, ethyl, butyl, chlorine atom, bromine atom or fluorine atom. $R^5$ is preferably carboxyl, methoxycarbonyl or ethoxycarbonyl.

The compound of the present invention encompasses those having an asymmetric carbon and existing as stereoisomers. These compounds may be resolved into purer isomers by conventional methods.

Examples of the pharmaceutically acceptable salts of quinoline-3-acetic acid derivative of the formula (I) include salts of alkali metals such as lithium, sodium and potassium, salts of alkaline earth metals such as calcium, magnesium and beryllium, aluminum salt, and organic salts such as triethylamine and pyridine.

Representative compounds of the formula (I) of the present invention are as follows.

ethyl 1-(4,5,7-trifluorobenzothiazol-2-yl)methyl-2-oxo-1,2,3,4-tetrahydro- 1H-quinolin-3-ylacetate 1-(4,5,7-trifluorobenzothiazol-2-yl)methyl-2-oxo-1,2,3,4-tetrahydro- 1H-quinolin-3-ylacetic acid 1-(4,5-difluorobenzothiazol-2-yl)methyl-2-oxo-1,2,3,4-tetrahydro- 1H-quinolin-3-ylacetic acid 1-(5,7-difluorobenzothiazol-2-yl)methyl-2-oxo-1,2,3,4-tetrahydro- 1H-quinolin-3-ylacetic acid ethyl 1-(4,7-difluorobenzothiazol-2-yl)methyl-2-oxo-1,2,3,4-tetrahydro- 1H-quinolin-3-ylacetate 1-(6,7-difluorobenzothiazol-2-yl)methyl-2-oxo-1,2,3,4-tetrahydro- 1H-quinolin-3-ylacetic acid 1-(4,5,7-trichlorobenzothiazol-2-yl)methyl-2-oxo-1,2,3,4-tetrahydro- 1H-quinolin-3-ylacetic acid ethyl 1-(4,5-dichlorobenzothiazol-2-yl)methyl-2-oxo-1,2,3,4-tetrahydro- 1H-quinolin-3-ylacetate 1-(5,7-dichlorobenzothiazol-2-yl)methyl-2-oxo-1,2,3,4-tetrahydro- 1H-quinolin-3-ylacetic acid 1-(4,7-dichlorobenzothiazol-2-yl)methyl-2-oxo-1,2,3,4-tetrahydro- 1H-quinolin-3-ylacetic acid 1-(6,7-dichlorobenzothiazol-2-yl)methyl-2-oxo-1,2,3,4-tetrahydro- 1H-quinolin-3-ylacetic acid ethyl 1-(4-fluorobenzothiazol-2-yl)methyl-2-oxo-1,2,3,4-tetrahydro- 1H-quinolin-3-ylacetate 1-(5-fluorobenzothiazol-2-yl)methyl-2-oxo-1,2,3,4-tetrahydro-1H-quinolin- 3-ylacetic acid 1-(7-fluorobenzothiazol-2-yl)methyl-2-oxo-1,2,3,4-tetrahydro-1H-quinolin- 3-ylacetic acid 1-(4-chlorobenzothiazol-2-yl)methyl-2-oxo-1,2,3,4-tetrahydro-1H-quinolin- 3-ylacetic acid 1-(5-chlorobenzothiazol-2-yl)methyl-2-oxo-1,2,3,4-tetrahydro-1H-quinolin- 3-ylacetic acid 1-(7-chlorobenzothiazol-2-yl)methyl-2-oxo-1,2,3,4-tetrahydro-1H-quinolin- 3-ylacetic acid ethyl 1-(4-bromobenzothiazol-2-yl)methyl-2-oxo-1,2,3,4-tetrahydro- 1H-quinolin-3-ylacetate 1-(5-bromobenzothiazol-2-yl)methyl-2-oxo-1,2,3,4-tetrahydro-1H-quinolin- 3-ylacetic acid 7-chloro-1-(4,5,7-trifluorobenzothiazol-2-yl)methyl-2-oxo-1,2,3,4-tetrahydro-1H-quinolin-3-yl acetic acid 6-chloro-1-(4,5,7-trifluorobenzothiazol-2-yl)methyl-2-oxo-1,2,3,4-tetrahydro-1H-quinolin-3-yl acetic acid 6-fluoro-1-(4,5,7-trifluorobenzothiazol-2-yl)methyl-2-oxo-1,2,3,4-tetrahydro-1H-quinolin-3-ylacetic acid ethyl 7-fluoro-1-(4,5,7-trifluorobenzothiazol-2-yl)methyl-2-oxo- 1,2,3,4-tetrahydro-1H-quinolin-3-ylacetate 5-fluoro-1-(4,5,7-trifluorobenzothiazol-2-yl)methyl-2-oxo-1,2,3,4-tetrahydro-1H-quinolin-3-ylacetic acid ethyl 1-(4,5,7-trifluorobenzothiazol-2-yl)methyl-5-methyl-2-oxo- 1,2,3,4-tetrahydro-1H-quinolin-3-ylacetate 1-(4,5,7-trifluorobenzothiazol-2-yl)methyl-6-methyl-2-oxo-1,2,3,4-tetrahydro-1H-quinolin-3-ylacetic acid 1-(4,5,7-trifluorobenzothiazol-2-yl)methyl-7-methyl-2-oxo-1,2,3,4-tetrahydro-1H-quinolin-3-ylacetic acid ethyl 1-(4,5,7-trifluorobenzothiazol-2-yl)methyl-7-methyl-2-oxo- 1,2,3,4-tetrahydro-1H-quinolin-3-ylacetate 5-chloro-1-(4,5-difluorobenzothiazol-2-yl)methyl-2-oxo-1,2,3,4-tetrahydro- 1H-quinolin-3-ylacetate acid 6-chloro-1-(4,5-difluorobenzothiazol-2-yl)methyl-2-oxo-1,2,3,4-tetrahydro- 1H-quinolin-3-ylacetate acid 7-chloro-1-(4,5-difluorobenzothiazol-2-yl)methyl-2-oxo-1,2,3,4-tetrahydro- 1H-quinolin-3-ylacetic acid ethyl 8-chloro-1-(4,5-difluorobenzothiazol-2-yl)methyl-2-oxo- 1,2,3,4-tetrahydro-1H-quinolin-3-ylacetate 5-fluoro-1-(4,5-difluorobenzothiazol-2-yl)methyl-2-oxo-1,2,3,4-tetrahydro- 1H-quinolin-3-ylacetic acid 6-fluoro-1-(4,5-difluorobenzothiazol-2-yl)methyl-2-oxo-1,2,3,4-tetrahydro- 1H-quinolin-3-ylacetic acid 7-fluoro-1-(4,5-difluorobenzothiazol-2-yl)methyl-2-oxo-1,2,3,4-tetrahydro- 1H-quinolin-3-ylacetic acid ethyl 8-fluoro-1-(4,5-difluorobenzothiazol-2-yl)methyl-2-oxo- 1,2,3,4-tetrahydro-1H-quinolin-3-ylacetate 1-(4,5-difluorobenzothiazol-2-yl)methyl-5-methyl-2-oxo-1,2,3,4-tetrahydro- 1H-quinolin-3-ylacetic acid 1-(4,5-difluorobenzothiazol-2-yl)methyl-6-methyl-2-oxo-1,2,3,4-tetrahydro- 1H-quinolin-3-ylacetic acid ethyl 1-(4,5-difluorobenzothiazol-2-yl)methyl-6-methyl-2-oxo- 1,2,3,4-tetrahydro-1H-quinolin-3-ylacetate ethyl 1-(4,5-difluorobenzothiazol-2-yl)methyl-7-methyl-2-oxo- 1,2,3,4-tetrahydro-1H-quinolin-3-ylacetate 5-bromo-1-(4,5-difluorobenzothiazol-2-yl)methyl-2-oxo-1,2,3,4-tetrahydro- 1H-quinolin-3-ylacetate acid 6-bromo-1-(4,5-difluorobenzothiazol-2-yl)methyl-2-oxo-1,2,3,4-tetrahydro- 1H-quinolin-3-ylacetate acid ethyl 7-bromo-1-(4,5-difluorobenzothiazol-2-yl)methyl-2-oxo- 1,2,3,4-tetrahydro-1H-quinolin-3-ylacetate 6-ethyl-1-(4,5-difluorobenzothiazol-2-yl)methyl-2-oxo-1,2,3,4-tetrahydro- 1H-quinolin-3-ylacetic acid ethyl 7-ethyl-1-(4,5-difluorobenzothiazol-2-yl)methyl-2-oxo- 1,2,3,4-tetrahydro-1H-quinolin-3-ylacetate 5-ethyl-1-(4,5,7-trifluorobenzothiazol-2-yl)methyl-2-oxo-1,2,3,4-tetrahydro-1H-quinolin-3-ylacetic acid 6-ethyl-1-(4,5,7-trifluorobenzothiazol-2-yl)methyl-2-oxo-1,2,3,4-tetrahydro-1H-quinolin-3-ylacetic acid 7-ethyl-1-(4,5,7-trifluorobenzothiazol-2-yl)methyl-2-oxo-1,2,3,4-tetrahydro-1 H-quinolin-3-ylacetic acid 6-butyl-1-(4,5,7-trifluorobenzothiazol-2-yl)methyl-2-oxo-1,2,3,4-tetrahydro-1 H-quinolin-3-ylacetic acid ethyl 7-butyl-1-(4,5,7-trifluorobenzothiazol-2-yl)methyl-2-oxo- 1,2,3,4-tetrahydro-1H-quinolin-3-ylacetate 5-bromo-1-(4,5,7-trifluorobenzothiazol-2-yl)methyl-2-oxo- 1,2,3,4-tetrahydro-1H-quinolin-3-ylacetic acid 6-bromo-1-(4,5,7-trifluorobenzothiazol-2-yl)methyl-2-oxo- 1,2,3,4-tetrahydro-1H-quinolin-3-ylacetic acid ethyl 7-bromo-1-(4,5,7-trifluorobenzothiazol-2-yl)methyl-2-oxo- 1,2,3,4-tetrahydro-1H-quinolin-3-ylacetate 6-chloro-1-(4,7-difluorobenzothiazol-2-yl)methyl-2-oxo-1,2,3,4-tetrahydro- 1H-quinolin-3-ylacetate acid 7-chloro-1-(4,7-difluorobenzothiazol-2-yl)methyl-2-oxo-1,2,3,4-tetrahydro- 1H-quinolin-3-ylacetate acid 5-chloro-1-(5,7-difluorobenzothiazol-2-yl)methyl-2-oxo-1,2,3,4-tetrahydro- 1H-quinolin-3-ylacetic acid ethyl 6-chloro-1-(5,7-difluorobenzothiazol-2-yl)methyl-2-oxo- 1,2,3,4-tetrahydro-1H-quinolin-3-ylacetate 7-chloro-1-(5,7-difluorobenzothiazol-2-yl)methyl-2-oxo-1,2,3,4-tetrahydro- 1H-quinolin-3-ylacetic acid 6-fluoro-1-(5,7-difluorobenzothiazol-2-yl)methyl-2-oxo-1,2,3,4-tetrahydro- 1H-quinolin-3-ylacetic acid
ethyl 7-fluoro-1-(5,7-difluorobenzothiazol-2-yl)methyl-2-oxo- 1,2,3,4-tetrahydro-1H-quinolin-3-ylacetate
1-(5,7-difluorobenzothiazol-2-yl)methyl-6-methyl-2-oxo-1,2,3,4-tetrahydro- 1H-quinolin-3-ylacetic acid
1-(5,7-difluorobenzothiazol-2-yl)methyl-7-methyl-2-oxo-1,2,3,4-tetrahydro- 1H-quinolin-3-ylacetic acid
6-chloro-1-(6,7-difluorobenzothiazol-2-yl)methyl-2-oxo-1,2,3,4-tetrahydro- 1H-quinolin-3-ylacetic acid
ethyl 7-chloro-1-(6,7-difluorobenzothiazol-2-yl)methyl-2-oxo- 1,2,3,4-tetrahydro-1H-quinolin-3-ylacetate
6-fluoro-1-(6,7-difluorobenzothiazol-2-yl)methyl-2-oxo-1,2,3,4-tetrahydro- 1H-quinolin-3-ylacetic acid
1-(6,7-difluorobenzothiazol-2-yl)methyl-6-methyl-2-oxo-1,2,3,4-tetrahydro- 1H-quinolin-3-ylacetic acid
ethyl 1-(6,7-difluorobenzothiazol-2-yl)methyl-6-methyl-2-oxo- 1,2,3,4-tetrahydro-1H-quinolin-3-ylacetate
6-chloro-1-(4-fluorobenzothiazol-2-yl)methyl-2-oxo-1,2,3,4-tetrahydro- 1H-quinolin-3-ylacetic acid
ethyl 7-fluoro-1-(4-fluorobenzothiazol-2-yl)methyl-2-oxo-1,2,3,4-tetrahydro-1H-quinolin-3-ylacetate
1-(4-fluorobenzothiazol-2-yl)methyl-6-methyl-2-oxo-1,2,3,4-tetrahydro- 1H-quinolin-3-ylacetic acid
ethyl 1-(4-fluorobenzothiazol-2-yl)methyl-2-oxo-1,2,3,4-tetrahydro- 1H-quinolin-3-ylacetate
1-(4,5,7-trifluorobenzothiazol-2-yl)methyl-7-methyl-2-oxo-1,2,3,4-tetrahydro-1H-quinolin-3-ylacetic acid
6-chloro-1-(5-fluorobenzothiazol-2-yl)methyl-2-oxo-1,2,3,4-tetrahydro- 1H-quinolin-3-ylacetic acid
7-chloro-1-(5-fluorobenzothiazol-2-yl)methyl-2-oxo-1,2,3,4-tetrahydro- 1H-quinolin-3-ylacetic acid
6-fluoro-1-(5-fluorobenzothiazol-2-yl)methyl-2-oxo-1,2,3,4-tetrahydro- 1H-quinolin-3-ylacetic acid
ethyl 1-(5-fluorobenzothiazol-2-yl)methyl-6-methyl-2-oxo- 1,2,3,4-tetrahydro-1H-quinolin-3-ylacetate
6-methyl-1-(4,5,7-trichlorobenzothiazol-2-yl)methyl-7-methyl-2- oxo- 1,2,3,4-tetrahydro-1H-quinolin-3-ylacetic acid
ethyl 6-chloro-1-(4,5-dichlorobenzothiazol-2-yl)methyl-2-oxo- 1,2,3,4-tetrahydro-1H-quinolin-3-ylacetate
methyl 7-chloro-1-(4,5-dichlorobenzothiazol-2-yl)methyl-2-oxo- 1,2,3,4-tetrahydro-1H-quinolin-3-ylacetate
7-fluoro-1-(4,5-dichlorobenzothiazol-2-yl)methyl-2-oxo-1,2,3,4-tetrahydro- 1H-quinolin-3-ylacetic acid
1-(4,5-dichlorobenzothiazol-2-yl)methyl-7-methyl-2-oxo-1,2,3,4-tetrahydro- 1H-quinolin-3-ylacetic acid
ethyl 1-(5,7-dichlorobenzothiazol-2-yl)methyl-6-methyl-2-oxo- 1,2,3,4-tetrahydro-1H-quinolin-3-ylacetate
7-chloro-1-(4-chlorobenzothiazol-2-yl)methyl-2-oxo-1,2,3,4-tetrahydro- 1H-quinolin-3-ylacetic acid
6-fluoro-1-(4-chlorobenzothiazol-2-yl)methyl-2-oxo-1,2,3,4-tetrahydro- 1H-quinolin-3-ylacetic acid
6-fluoro-1-(5-chlorobenzothiazol-2-yl)methyl-2-oxo-1,2,3,4-tetrahydro- 1H-quinolin-3-ylacetic acid
1-(5-chlorobenzothiazol-2-yl)methyl-6-methyl-2-oxo-1,2,3,4-tetrahydro- 1H-quinolin-3-ylacetic acid
7-chloro-1-(4-bromobenzothiazol-2-yl)methyl-2-oxo-1,2,3,4-tetrahydro- 1H-quinolin-3-ylacetic acid
6-fluoro-1-(4-bromobenzothiazol-2-yl)methyl-2-oxo-1,2,3,4-tetrahydro- 1H-quinolin-3-ylacetic acid
6-chloro-1-(5-bromobenzothiazol-2-yl)methyl-2-oxo-1,2,3,4-tetrahydro- 1H-quinolin-3-ylacetic acid
1-(5-bromobenzothiazol-2-yl)methyl-6-methyl-2-oxo-1,2,3,4-tetrahydro- 1H-quinolin-3-ylacetic acid
ethyl 1-(4,5,7-trifluorobenzothiazol-2-yl)methyl-2-oxo-1,2-dihydro- 1H-quinolin-3-ylacetate
1-(4,5,7-trifluorobenzothiazol-2-yl)methyl-2-oxo-1,2-dihydro-1H-quinolin- 3-ylacetic acid
1-(4,5-difluorobenzothiazol-2-yl)methyl-2-oxo-1,2-dihydro-1H-quinolin- 3-ylacetic acid
1-(5,7-difluorobenzothiazol-2-yl)methyl-2-oxo-1,2-dihydro-1H-quinolin- 3-ylacetic acid
ethyl 1-(4,7-difluorobenzothiazol-2-yl)methyl-2-oxo-1,2-dihydro- 1H-quinolin-3-ylacetate
1-(6,7-difluorobenzothiazol-2-yl)methyl-2-oxo-1,2-dihydro-1H-quinolin- 3-ylacetic acid
1-(4,5,7-trichlorobenzothiazol-2-yl)methyl-2-oxo-1,2-dihydro-1H-quinolin- 3-ylacetic acid
ethyl 1-(4,5-dichlorobenzothiazol-2-yl)methyl-2-oxo-1,2-dihydro- 1H-quinolin-3-ylacetate
1-(5,7-dichlorobenzothiazol-2-yl)methyl-2-oxo-1,2-dihydro-1H-quinolin- 3-ylacetic acid
1-(4,7-dichlorobenzothiazol-2-yl)methyl-2-oxo-1,2-dihydro-1H-quinolin- 3-ylacetic acid
1-(6,7-dichlorobenzothiazol-2-yl)methyl-2-oxo-1,2-dihydro-1H-quinolin- 3-ylacetic acid
ethyl 1-(4-fluorobenzothiazol-2-yl)methyl-2-oxo-1,2-dihydro-1H-quinolin- 3-ylacetate
1-(5-fluorobenzothiazol-2-yl)methyl-2-oxo-1,2-dihydro-1H-quinolin- 3-ylacetic acid
1-(7-fluorobenzothiazol-2-yl)methyl-2-oxo-1,2-dihydro-1H-quinolin- 3-ylacetic acid
1-(4-chlorobenzothiazol-2-yl)methyl-2-oxo-1,2-dihydro-1H-quinolin- 3-ylacetic acid
1-(5-chlorobenzothiazol-2-yl)methyl-2-oxo-1,2-dihydro-1H-quinolin- 3-ylacetic acid
1-(7-chlorobenzothiazol-2-yl)methyl-2-oxo-1,2-dihydro-1H-quinolin- 3-ylacetic acid
ethyl 1-(4-bromobenzothiazol-2-yl)methyl-2-oxo-1,2-dihydro-1H-quinolin- 3-ylacetate
1-(5-bromobenzothiazol-2-yl)methyl-2-oxo-1,2-dihydro-1H-quinolin- 3-ylacetic acid
7-chloro-1-(4,5,7-trifluorobenzothiazol-2-yl)methyl-2-oxo-1,2-dihydro- 1H-quinolin-3-ylacetic acid
6-chloro-1-(4,5,7-trifluorobenzothiazol-2-yl)methyl-2-oxo-1,2-dihydro- 1H-quinolin-3-ylacetic acid
6-fluoro-1-(4,5,7-trifluorobenzothiazol-2-yl)methyl-2-oxo-1,2-dihydro- 1H-quinolin-3-ylacetic acid
ethyl 7-fluoro-1-(4,5,7-trifluorobenzothiazol-2-yl)methyl-2-oxo- 1,2-dihydro-1H-quinolin-3-ylacetate
5-fluoro-1-(4,5,7-trifluorobenzothiazol-2-yl)methyl-2-oxo-1,2-dihydro- 1H-quinolin-3-ylacetic acid
ethyl 1-(4,5,7-trifluorobenzothiazol-2-yl)methyl-5-methyl-2-oxo- 1,2-dihydro-1H-quinolin-3-ylacetate
1-(4,5,7-trifluorobenzothiazol-2-yl)methyl-6-methyl-2-oxo-1,2-dihydro- 1H-quinolin-3-ylacetic acid
1-(4,5,7-trifluorobenzothiazol-2-yl)methyl-7-methyl-2-oxo-1,2-dihydro- 1H-quinolin-3-ylacetic acid
ethyl 1-(4,5,7-trifluorobenzothiazol-2-yl)methyl-7-methyl-2-oxo- 1,2-dihydro-1H-quinolin-3-ylacetate
5-chloro-1-(4,5-difluorobenzothiazol-2-yl)methyl-2-oxo-1,2-dihydro- 1H-quinolin-3-ylacetic acid
6-chloro-1-(4,5-difluorobenzothiazol-2-yl)methyl-2-oxo-1,2-dihydro- 1H-quinolin-3-ylacetic acid
7-chloro-1-(4,5-difluorobenzothiazol-2-yl)methyl-2-oxo-1,2-dihydro- 1H-quinolin-3-ylacetic acid
ethyl 8-chloro-1-(4,5-difluorobenzothiazol-2-yl)methyl-2-oxo- 1,2-dihydro-1H-quinolin-3-ylacetate The process for producing the compound of the formula (I) of the present invention is described in detail in the following.

That is, a compound of the formula (II)

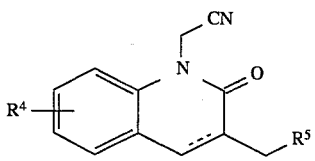

wherein $R^4$, $R^5$ and the broken line are as defined above, or a salt thereof [preferably a pharmaceutically acceptable salt of quinoline-3-acetic acid derivative of the formula (I)] is reacted with a compound of the formula (III)

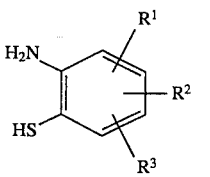

wherein $R^1$, $R^2$ and $R^3$ are as defined above, or an acid addition salt thereof in a suitable solvent. The reaction proceeds in the presence or absence of a solvent. The present reaction is preferably carried out in the presence of a strong acid such as hydrochloric acid or sulfuric acid.

After the reaction, the obtained compound may be subjected to hydrolysis in the presence of a base or an acid, if necessary.

As mentioned above, the above reaction is carried out in the presence or absence of a solvent. Examples of the solvent to be used for this reaction include alcohols such as methanol, ethanol and propanol. In this case, the reaction proceeds at 20°–200° C., preferably from 60° C. to a refluxing temperature.

When the solvent is not used, the compound of the formula (II) or a salt thereof (potassium salt etc.) may be reacted with an acid addition salt (hydrochloride etc.) of the formula (III) by melting them at 90°–250° C., preferably 130°–180° C.

Examples of the preferable base to be used for the hydrolysis include alkali metal hydroxides such as sodium hydroxide and potassium hydroxide, and alkali metal carbonates such as sodium carbonate and potassium carbonate. Preferred as the acid are organic acids such as formic acid, acetic acid, propionic acid, trifluoroacetic acid, benzenesulfonic acid and p-toluenesulfonic acid, and inorganic acids such as hydrochloric acid, hydrobromic acid, sulfuric acid and phosphoric acid.

The hydrolysis is generally carried out in a conventional solvent which does not adversely affect the reaction, such as water, acetone, dioxane, dichloromethane, methanol, ethanol, propanol, pyridine or N,N-dimethylformamide or a mixture thereof. The base or acid to be used for this reaction is liquid, it may be used as a solvent.

The reaction temperature is subject to no particular limitation and the reaction proceeds under cooling to under heating.

The starting compound of the formula (II) above is obtained by reacting a compound of the formula (IV)

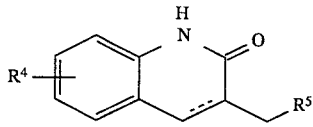

wherein $R^4$, $R^5$ and the broken line are as defined above, or a salt thereof [preferably a salt similar to the pharmaceutically acceptable salt of quinoline-3-acetic acid derivative of the formula (I)] with a compound of the formula (V)

$$Z\text{-}CH_2CN \quad (V)$$

wherein Z is a halogen atom (exemplified by those mentioned above). The reaction is preferably carried out in the presence of a suitable base under an inert gas atmosphere, if necessary.

Examples of the base mentioned above include inorganic bases such as alkali metal hydrides (e.g. sodium hydride), alkaline earth metal hydrides (e.g. calcium hydride), alkali metal hydroxides (e.g. sodium hydroxide, potassium hydroxide), alkali metal carbonates (e.g. sodium carbonate, potassium carbonate), alkali metal hydrogencarbonates (e.g. sodium hydrogencarbonate, potassium hydrogencarbonate), alkali metal alkoxides (e.g. sodium methoxide, sodium ethoxide, potassium t-butoxide), and alkali metal salts of alkanoic acid (e.g. sodium acetate).

The halogen atom as used herein is particularly preferably chlorine atom or bromine atom. The inert gas is exemplified by argon and nitrogen.

The above-mentioned reaction is generally carried out in various conventional solvents which do not exert adverse influence on the reaction, such as dichloromethane, methanol, ethanol, propanol, pyridine, N,N-dimethylformamide, tetrahydrofuran, dimethylsulfoxide or a mixture of these. Particularly preferred are N,N-dimethylformamide, tetrahydrofuran and dimethylsulfoxide. While the reaction temperature is not particularly limited, it is 0°–150° C., preferably from room temperature to 100° C.

The starting compound of the formula (III) is known or can be easily produced by a known method [Journal of Medicinal Chemistry, 34, 108–122 (1991)].

The starting compound of the formula (IV) is known or can be easily produced by a known method [Journal of American Chemical Society, 77, 5932–5933 (1955), Z. Naturforsch., Teil B, 28, 551–553 (1973)].

The compound of the present invention thus produced can be separated and purified by a conventional method such as extraction, precipitation, fractional chromatography, partition, crystallization and recrystallization.

The compound of the present invention thus produced can be converted to a pharmaceutically acceptable salt as desired by a conventional method.

The pharmacological test to show the effectiveness of the compound of the formula (I) of the present invention and the results are given in the following. The similar results were also obtained with regard to the compounds of the present invention that are not exemplified here.

1) Aldose reductase inhibitory action

Preparation of Enzyme

An aldose reductase enzyme standard product was prepared from swine lens according to the method of S. Hayman et al. [Journal of Biological Chemistry, 240, 877–882 (1965)]. That is, swine lenses freeze-stored at −80° C. were homogenized with distilled water and cetrifuged at 10,000 g for 15 minutes. The supernatant was prepared into a 40% ammonium sulfate solution and subjected to cetrifugation at 10,000 g for 10 minutes. The supernatant obtained was dialyzed overnight against a 0.05M sodium chloride solution to give a dialyzed solution, which was used as an enzyme standard product.

Activity Determination

The activity of aldose reductase was determined by the above-mentioned method of S. Hayman et al. That is, the above-mentioned enzyme solution (25 μl) and a drug solution (25 μl) in 1% DMSO at various concentrations were added to a 40 mM phosphate buffer (200 μl, pH 6.2) containing final concentrations of 0.4M lithium sulfate, 0.1 mM NADPH (reduced type nicotinamide adenine dinucleotide phosphate) and 3 mM diglyceraldehyde as a substrate. The mixture was allowed to react at 25° C. for 2 minutes and the changes in absorbance at 340 nm was determined with COBAS FARA II (manufactured by Roche).

The changes in absorbance when 1% DMSO was added instead of the drug solution was taken as 100%, based on which 50% inhibition concentration ($IC_{50}$) was calculated and shown in Table 1.

In the Table, $IC_{50}$ (M) shows the concentration of the compound of the present invention inhibiting the aldose reductase activity by 50%. The test drug number indicates the example number to be mentioned later. Compound A is 3,4-dihydro- 2,8-diisopropyl-3-thioxo-2H-1,4-benzoxazine-4-acetic acid disclosed in Japanese Patent Unexamined Publication 107970/1988.

TABLE 1

| Test drug | $IC_{50}$ (M) |
|---|---|
| Example 11 | $9.0 \times 10^{-9}$ |
| Example 12 | $1.3 \times 10^{-8}$ |
| Example 17 | $1.1 \times 10^{-8}$ |
| Example 19 | $1.2 \times 10^{-8}$ |
| Example 20 | $9.4 \times 10^{-9}$ |
| Compound A | $2.1 \times 10^{-8}$ |

2) Inhibitory action on sorbitol accumulation in tissues of rats with experimental diabetes Sprague-Dawley rats (male, 6 weeks old, 5–6 per group) were fasted for 18 hours and injected with streptozotocin (SIGMA, 60 mg/kg) via the tail vein under etherization to prepare rats with diabetes.

The compound was orally administered at 4, 8 and 24 hours after the injection of streptozotocin at 10 mg/kg as a 0.5% carboxymethylcellulose suspension. During the administrations, the rats were raised under free access to feed and water and the sorbitol content in the tissues (erythrocytes, sciatic nerve, lens) was determined 3 hours after the final administration according to the enzyme method of H. Y. Bergmeyer et al. [Methods of Enzymatic Analysis, vol. 3, 1323–1330 (1974)] with the use of SDH (sorbitol dehydrogenase) and NAD (β-nicotinamide adenine dinucleotide). The results are expressed in percent (%) relative to the value of a control group administered with 0.5% carboxymethylcellulose solution (solvent) instead of the compound, which was taken as 100%. The results are shown in Table 2.

TABLE 2

| | Sorbitol accumulation (%)[1] | | |
|---|---|---|---|
| Test compound | erythrocytes | sciatic nerve | lens |
| Example 11 | 15.6** | 0.0** | 50.7** |
| Example 12 | 0.0** | 0.0** | 78.8 |
| Example 17 | 31.2** | 0.5** | 46.9** |
| Compound A (30 mg/kg) | 53.7** | 54.9** | 87.3 |

Note:
[1] The control was taken as 100%.
*Tukey's Multiple Range Test, $p < 0.05$
**Tukey's Multiple Range Test, $p < 0.01$ The acute toxicity (safety) of the compound of the present invention was confirmed by the following method.

Normal ICR mice (male, 7 weeks old, 5 per group) were fasted for 18 hours and the compounds (300 mg/kg) of Example 11 and Example 20 were orally administered as 0.5% carboxymethylcellulose suspensions. To the control group, a 0.5% carboxymethylcellulose solution alone was orally administered and observation was continued for 14 days thereafter, during which period the mice were allowed to take feed and water freely.

The result showed no case of death of the mice administered with the compounds of Example 11 or Example 20 and their weights showed transition in the same manner as in the control group.

The compound of the present invention has a superior aldose reductase inhibitory action on mammals inclusive of human, cow, horse, dog, mouse, rat and so on and shows superior safety. Accordingly, it is effectively used for the prevention and/or treatment of the complications of diabetes, such as faulty union of corneal injury, diabetic neurosis, nephropathy, retinopathy and cataract. When the compound of the present invention is administered for the prevention and/or treatment of the above-mentioned diseases, oral or parenteral administration can be employed.

The pharmaceutical composition containing the compound of the present invention is provided in the form of a solid preparation, semi-solid preparation or liquid preparation together with organic or inorganic carrier and/or excipient suitable for external, oral or local administration. The compound of the present invention is prepared into a dosage form such as tablet, pellet, capsule, suppository, liquid, emulsion or suspension along with nontoxic and pharmacologically acceptable auxiliary ingredients. The auxiliary ingredients include those effectively used for the production of solid, semi-solid or liquid preparation, such as water, glucose, lactose, gelatin, mannitol, starch paste, magnesium trisillicate, corn starch, keratin, colloidal silica, potato starch and urea. In addition, the auxiliary ingredients include stabilizer, extender, coloring and aromatic agent. So as to retain the activity of the compound of the present invention, a preservative may be also contained. The pharmaceutical preparation should contain the compound of the present invention in an amount sufficient to produce the desired therapeutic effect against the progress or symptom of the target diseases.

When the compound of the present invention is administered to human, it is administered, for example, parenterally (e.g. preferably by injection or eye drop) or orally in an amount sufficient to inhibit aldose reductase or an amount sufficient to prevent and/or treat the complications of diabetes. While the effective amount of the compound of the present invention varies depending on age, body weight, symptom, therapeutic effect, administration route, administration period etc., it is generally administered orally at 1–2000 mg/day, preferably at 10–600 mg/day in a single to thrice divided doses a day.

The pharmaceutical composition of the present invention contains the compound of the present invention and hence is effective as an aldose reductase inhibitor and for the prevention and/or treatment of the complications of diabetes, such as faulty union of corneal injury, diabetic neurosis, nephropathy, retinopathy and cataract, as mentioned above.

An administration of the compound of the present invention in an effective amount to mammals such as human results in inhibition of aldose reductase activity, which ultimately results in the prevention and/or treatment of the complications of diabetes such as faulty union of corneal injury, diabetic neurosis, nephropathy, retinopathy and cataract.

The present invention is explained in more detail in the following by way of examples and reference examples, to which the present invention is not limited.

REFERENCE EXAMPLE 1

Production of Ethyl
1-Cyanomethyl-2-Oxo-1,2,3,4-Tetrahydro-1H-Quinolin-3-ylacetate Sodium hydride (60% in mineral oil, 240 mg) was added to dimethylformamide (4 ml) and the mixture was dropwise added with ethyl 2-oxo-1,2,3,4-tetrahydro-1H-quinolin-3-ylacetate (1.17 g) in dimethylformamide (5 ml) while stirring under ice-cooling. The mixture was stirred for 30 minutes and thereto was dropwise added dimethylformamide (5 ml) containing bromoacetonitrile (720 mg). The mixture was stirred at room temperature for 3 hours. The reaction mixture was poured into an aqueous solution of ammonium chloride and the mixture was extracted with ethyl acetate.

The extract was washed with brine and dried over anhydrous magnesium sulfate. The solvent was distilled away and the residue was subjected to silica gel column chromatography eluting with methylene chloride to give 1.15 g of the title compound. The structural formula and the physical properties are shown in Table 3.

REFERENCE EXAMPLES 2 AND 3

In substantially the same manner, the reaction was carried out to give the compounds of Table 3.

The structural formulas and the physical properties of the compounds obtained in the Reference Examples and the compound of Reference Example 1 are shown in Table 3.

TABLE 3

| Ref. Ex. | $R^4$ | $R^5$ | NMR: δ | MS(EI) m/z |
|---|---|---|---|---|
| 1 | H | $COOC_2H_5$ | 1.29(3H, t), 2.52(1H, dd), 2.90–3.16(4H, m), 4.19(2H, q), 4.71(1H, d), 4.97(1H, d), 7.04–7.38 (4H, m) [$CDCl_3$] | 272$^{(M+)}$ 227 185 |
| 2 | 6-$CH_3$ | $COOCH_3$ | 2.33(3H, s), 2.52(1H, dd), 2.82–3.12(4H, m), 3.73(3H, s), 4.71(1H, d), 4.93(1H, d), 6.92–7.15 (3H, m) [$CDCl_3$] | 272$^{(M+)}$ 199 172 |
| 3 | 6-F | $COOCH_3$ | 2.55(1H, dd), 2.87–3.17 (4H, m), 3.74(3H, s), 4.71(1H, d), 4.94(1H, d), 6.95–7.06(3H, m) [$CDCl_3$] | 276$^{(M+)}$ 203 176 |

REFERENCE EXAMPLE 4

Production of Methyl
1-Cyanomethyl-2-Oxo-1,2-Dihydro-1H-Quinolin-3-ylacetate

Potassium-tert-butoxide (560 mg) was suspended in dimethylformamide (2 ml) and the suspension was stirred under ice-cooling. A solution of dimethylformamide (8 ml) containing methyl 2-oxo-1,2-dihydro-1H-quinolin-3-ylacetate (868 mg) was dropwise added to the compound and the mixture was stirred for 30 minutes. Then a solution of dimethylformamide (2 ml) containing bromoacetonitrile (530 mg) was dropwise added thereto. The mixture was stirred at room temperature for 3 hours and poured into an aqueous solution of ammonium chloride and the mixture was extracted with ethyl acetate.

The extract was dried over anhydrous magnesium sulfate and the solvent was distilled away. The residue was recrystallized from ethanol-ethyl acetate to give 185 mg of methyl 1-cyanomethyl-2-oxo-1,2-dihydro-1H-quinolin-3-ylacetate. The structural formula and the physical properties are shown in Table 4. In the following Tables, the substituent is hydrogen atom unless specifically indicated.

TABLE 4

| Ref. Ex. | $R^4$ | $R^5$ | NMR: δ | MS(EI) m/z |
|---|---|---|---|---|
| 4 | — | — | 3.67(2H, s), 3.75(3H, s), 5.28(2H, s), 7.31–7.38(2H, m), 760–7.67(2H, m), 7.75(1H, s) [$CDCl_3$] | 256$^{(M+)}$ 224 197 |

EXAMPLE 1

Production of Ethyl
1-(4,5,7-Trifluorobenzothiazol-2-yl)Methyl-2-Oxo-1,2,3,4-Tetrahydro-1H-Quinolin-3-ylacetate Ethyl 1-cyanomethyl-2-oxo-1,2,3,4-tetrahydro-1H-quinolin-3-ylacetate (544 mg) as obtained in Reference Example 1 and 2-amino- 3,4,6-trifluorothiophenol hydrochloride (474 mg) were added to anhydrous ethanol (4 ml) and the mixture was refluxed under heating under an argon atmosphere. Twenty-four hours later, the solvent was distilled away and water was added to the residue, followed by extraction with ethyl acetate.

The extract was dried over anhydrous magnesium sulfate. The solvent was distilled away and the residue was subjected to silica gel column chromatography eluting with methylene chloride-methanol to give 625 mg of the title compound. The structural formula and the physical properties are shown in Table 5.

TABLE 5

| Ex. No. | $R^1,R^2,R^3$ | $R^4$ | NMR: δ | MS(EI) m/z |
|---|---|---|---|---|
| 1 | 4,5,7-F | H | 1.30(3H, t), 2.58(1H, dd), 2.97–3.22(4H, m), 4.22(2H, q), 5.42(1H, d), | 434$^{(M+)}$ 389 347 |

TABLE 5-continued

Structure: benzothiazole-CH₂-N linked to tetrahydroquinolinone with CH₂COOC₂H₅ substituent (R¹ at 4, R² at 5/6, R³ at 7 of benzothiazole; R⁴ on quinoline aryl ring positions 5-8)

| Ex. No. | R¹,R²,R³ | R⁴ | NMR: δ | MS(EI) m/z |
|---|---|---|---|---|
| 2 | 4,5-F | H | 1.30(3H, t), 2.56(1H, dd), 2.97–3.23(4H, m), 4.21(2H, q), 5.41(1H, d), 5.70(1H, d), 7.00–7.07(1H, m), 7.18–7.29(4H, m), 7.45–7.51(1H, m) [CHCl₃] | 416$^{(M+)}$ 329 |
| 3 | 5,7-F | H | 1.30(3H, t), 2.57(1H, dd), 2.96–3.27(4H, m), 4.21(2H, q), 5.37(1H, d), 5.67(1H, d), 6.87–7.26(5H, m), 7.51–7.56(1H, m) [CDCl₃] | 416$^{(M+)}$ 371 329 |
| 4 | 6,7-F | H | 1.30(3H, t), 2.57(1H, dd), 2.95–3.27(4H, m), 4.21(2H, q), 5.36(1H, d), 5.65(1H, d), 7.02–7.38(5H, m), 7.71–7.75(1H, m) [CDCl₃] | 416$^{(M+)}$ 371 329 |
| 5 | 5-F | H | 1.30(3H, t), 2.56(1H, dd), 2.94–3.26(4H, m), 4.21(2H, q), 5.37(1H, d), 5.68(1H, d), 6.99–7.26(5H, m), 7.66–7.75(2H, m) [CDCl₃] | 398$^{(M+)}$ 353 311 |
| 6 | 5,7-Cl | H | 1.30(3H, t), 2.57(1H, dd), 2.95–3.26(4H, m), 4.21(2H, q), 5.34(1H, d), 5.67(1H, d), 7.01–7.26(4H, m), 7.38(1H, d), 7.90(1H, d) [CDCl₃] | 450$^{(M+)}$ 448 363 361 |
| 7 | 4,5,7-F | 6-CH₃ | 1.30(3H, t), 2.28(3H, s), 2.56(1H, dd), 2.88–3.21(4H, m), 4.21(2H, q), 5.42(1H, d), 5.64(1H, d), 6.97–7.07(4H, m) [CDCl₃] | 448$^{(M+)}$ 248 204 |
| 8 | 4,5-F | 6-CH₃ | 1.30(3H, t), 2.28(3H, s), 2.54(1H, dd), 2.87–3.18(4H, m), 4.21(2H, q), 5.41(1H, d), 5.65(1H, d), 7.00–7.28(4H, m), 7.44–7.50(1H, m) [CDCl₃] | 430$^{(M+)}$ 343 184 |
| 9 | 4,5,7-F | 6-F | 1.30(3H, t), 2.57(1H, dd), 2.88–3.23(4H, m), 4.21(2H, q), 5.38(1H, d), 5.65(1H, d), 6.87–7.22(4H, m) [CDCl₃] | 452$^{(M+)}$ 365 202 |

EXAMPLES 2–10

In substantially the same manner as in Example 1, the compounds of Table 5 and Table 6 were obtained.

The structural formulas and the physical properties of the compounds obtained in the Reference Examples and the compound of Example 1 are shown in Table 5 and Table 6.

TABLE 6

Structure: 4,5,7-trifluorobenzothiazol-2-yl-CH₂-N linked to quinolinone with =CH-COOC₂H₅

| Ref. Ex. | R¹, R² R³ | R⁴ | NMR: δ | MS(EI) m/z |
|---|---|---|---|---|
| 10 | — | — | 1.30(3H, t), 3.73(2H, s), 4.24(2H, q), 5.94(2H, s), 6.97–7.77(5H, m), 7.74(1H, s) [CDCl₃] | 432$^{(M+)}$ 386 329 |

EXAMPLE 11

Production of 1-(4,5,7-Trifluorobenzothiazol-2-Yl)Methyl-2-Oxo- 1,2,3,4-Tetrahydro-1H-Quinolin-3-Ylacetic Acid The compound (710 mg) obtained in Example 1 was added to a mixture (16.5 ml) of 2N sodium hydroxide-ethanol (1:10) and the mixture was stirred at room temperature for 3 hours. 1N Hydrochloric acid was added thereto to make the mixture acidic. The mixture was extracted with ethyl acetate and the ethyl acetate layer was washed with water and dried. The solvent was distilled away and the crude product obtained was recrystallized from ethyl acetate-isopropyl ether to give 580 mg of the title compound.

The structural formula and the physical properties of the compound are shown in Table 7.

TABLE 7

Structure: benzothiazole-CH₂-N linked to tetrahydroquinolinone with CH₂COOH substituent

| Ex. No. | R¹,R²,R³ | R⁴ | NMR: δ | IR(KBr) cm⁻¹ | MS(EI) m/z |
|---|---|---|---|---|---|
| 11 | 4,5,7-F | H | 2.67(1H, dd), 301–3.17(4H, m), 5.43(1H, d), 5.69(1H, d), 6.96–7.26(5H, m) [CDCl₃] | 2600–3400, 1710, 1670, 1510 | 406$^{(M+)}$ 347 |
| 12 | 4,5-F | H | 2.66(1H, dd), 3.00–3.15(4H, m), 5.42(1H, d), 5.71(1H, d), | 2600–3400, 1720, 1660, | 388$^{(M+)}$ 330 329 |

TABLE 7-continued

[Structure: quinoline-benzothiazole with R¹ (4), R² (5), R³ (7) on benzothiazole ring; R⁴ (6,7) on quinoline ring; N-CH₂ linker; COOH group at position 5]

| Ex. No. | R¹,R²,R³ | R⁴ | NMR: δ | IR(KBr): cm⁻¹ | MS(EI) m/z |
|---|---|---|---|---|---|
| 13 | 5,7-F | H | 7.02~7.08(1H, m), 7.16~7.29(4H, m), 7.43~7.49(1H, m) [CDCl₃] 2.66(1H, dd), 2.99~3.26(4H, m), 5.39(1H, d), 5.68(1H, d), 6.86~7.26(5H, m), 7.51~7.56(1H, m) | 1500 2550~ 3350, 1725, 1675, 1465, 1420 | 388$^{(M+)}$ 329 |
| 14 | 6,7-F | H | 2.67(1H, dd), 2.96~3.24(4H, m), 5.37(1H, d), 5.67(1H, d), 7.01~7.37(5H, m), 7.71~7.77(1H, m) [CDCl₃] | 2550~ 3350, 1730, 1670, 1500 | 388$^{(M+)}$ 329 183 |
| 15 | 5-F | H | 2.57(1H, dd), 2.96~3.25(4H, m), 5.41(1H, d), 5.66(1H, d), 7.01~7.26(5H, m), 7.64~7.80(2H, m) [CDCl₃—CD₃OD] | 2550~ 3400, 1725, 1680, 1465 | 370$^{(M+)}$ 311 283 |
| 16 | 5,7-Cl | H | 2.58(1H, dd), 2.96~3.25(4H, m), 5.37(1H, d), 5.66(1H, d), 7.02~7.28(4H, m), 7.40(1H, d), 7.91(1H, d) [CDCl₃—CD₃OD] | 2550~ 3400, 1730, 1675, 1435, 1410 | 422$^{(M+)}$ 420 363 361 |
| 17 | 4,5,7-F | 6-CH₃ | 2.28(3H, s), 2.65(1H, dd), 2.90~3.20(4H, m), 5.43(1H, d), 5.65(1H, d), 6.96~7.09(4H, m) [CDCl₃] | 2550~ 3400, 1720, 1680, 1510 | 420$^{(M+)}$ 361 |
| 18 | 4,5-F | 6-CH₃ | 2.27(3H, s), 2.55(1H, dd), 2.86~3.12(4H, m), 5.46(1H, d), 5.61(1H, d), 7.00~7.10(3H, m), 7.29~7.40(1H, m), 7.63~7.70(1H, m) [CD₃OD] | 2550~ 3350, 1720, 1655, 1505 | 430$^{(M+)}$ 343 184 |
| 19 | 4,5,7-F | 6-F | 2.67(1H, dd), 2.91~3.34(4H, m) 5.38(1H, d), 5.67(1H, d), 6.89~7.25(4H, m) [CDCl₃] | 2550~ 3400, 1730, 1670, 1505 | 424$^{(M+)}$ 365 |

EXAMPLES 12–20

In substantially the same manner as in Example 11, the compounds of Table 7 and Table 8 were obtained.

The structural formulas and the physical properties of the compounds obtained in these Examples and the compound of Example are shown in Table 7 and Table 8.

TABLE 8

[Structure: 4,5,7-trifluoro benzothiazole connected via N-CH₂ to quinolinone with COOH group; 6-F on quinoline ring]

| Ref. Ex. | R¹, R² R³ | R⁴ | NMR: δ | IR(KBr): cm⁻¹ | MS(EI) m/z |
|---|---|---|---|---|---|
| 20 | — | — | 3.67(2H, s), 5.92(2H, s), 7.05~7.70(5H, m), 7.82(1H, s) [CDCl₃] | 2600– 3400, 1725, 1650, 1600, 1530 | 404$^{(M+)}$ 360 329 |

The formulation examples of the pharmaceutical composition for treating the complications of diabetes, which contains the quinoline-3-acetic acid derivative of the present invention as an active ingredient, are given in the following.

FORMULATION EXAMPLE 1

| | |
|---|---|
| Compound of Example 11 | 20 g |
| Lactose | 315 g |
| Corn starch | 125 g |
| Crystalline cellulose | 25 g |

The above ingredients were homogeneously mixed and added with an aqueous solution of 7.5% hydroxypropylcellulose (200 ml). The mixture was prepared into granules by an extrusion granulator with the use of a 0.5 mm diameter screen. The granules were immediately rounded and dried. The dry granules were coated with a film coating solution (1.9 kg) of the following composition by a fluid-type granulator to give enteric coated granules.

| Coating solution: | |
|---|---|
| Hydroxypropylmethylcellulose phthalate | 5.0 (w/w) % |
| Stearic acid | 0.25 (w/w) % |
| Methylene chloride | 50.0 (w/w) % |
| Ethanol | 44.75 (w/w) % |

FORMULATION EXAMPLE 2

| | |
|---|---|
| Compound of Example 20 | 20 g |
| Lactose | 100 g |
| Corn starch | 36 g |
| Crystalline cellulose | 30 g |
| Calcium carboxymethylcellulose | 10 g |
| Magnesium stearate | 4 g |

The above ingredients were homogeneously mixed and prepared by a single punch tableting machine into tablets each weighing 200 mg with the use of a 7.5 mm diameter punch. Then, the film coating solution of the following composition was spray-coated at 10 mg per tablet to give enteric coated tablets.

| Coating solution: | |
|---|---|
| Hydroxypropylmethylcellulose phthalate | 8.0 (w/w) % |
| Glycerol fatty acid ester | 0.4 (w/w) % |
| Methylene chloride | 50.0 (w/w) % |
| White beewax | 0.1 (w/w) % |
| Isopropanol | 41.5 (w/w) % |

FORMULATION EXAMPLE 3

| Compound of Example 1 | 200 g |
|---|---|
| Polysorbate 80 | 20 g |
| PANASETO ® 810 | 1780 g |

The above ingredients were mixed for complete dissolution. With the use of a film solution for soft capsules composed of gelatin (100 parts), con. glycerine (30 parts), ethyl p-hydroxybenzoate (0.4 part) and propyl p-hydroxybenzoate (0.2 part), soft capsules containing 200 mg of a drug solution per capsule were prepared by a rotary method.

FORMULATION EXAMPLE 4

| Compound of Example 20 | | 100 mg |
|---|---|---|
| Sodium acetate | | 2 mg |
| Acetic acid (for adjusting to pH 5.8) | | suitable amount |
| Distilled water | | residual amount |
| | Total | 10 ml/vial |

An injection having the above formulation was prepared by a conventional method.

FORMULATION EXAMPLE 5

| Compound of Example 20 | | 0.05 g |
|---|---|---|
| Polysorbate 80 | | 0.2 g |
| Sodium dihydrogenphosphate 2 hydrate | | 0.2 g |
| Disodium hydrogenphosphate 12 hydrate | | 0.5 g |
| Sodium chloride | | 0.75 g |
| Methyl p-hydroxybenzoate | | 0.026 g |
| Propyl p-hydroxybenzoate | | 0.014 g |
| Sterile purified water | | suitable amount |
| | Total | 100 ml |

An eye drop having the above formulation was prepared by a conventional method.

INDUSTRIAL UTILIZATION

The novel compound, quinoline-3-acetic acid derivative of the formula (I), and a pharmaceutically acceptable salt thereof of the present invention have an aldose reductase inhibitory activity in mammals inclusive of human and have superior safety. Accordingly, they are useful as pharmaceutical compositions for the treatment of the complications of diabetes, such as faulty union of corneal injury, cataract, neurosis, retinopathy and nephropathy, particularly cataract and neurosis.

We claim:
1. A quinoline-3-acetic acid derivative of the formula (I)

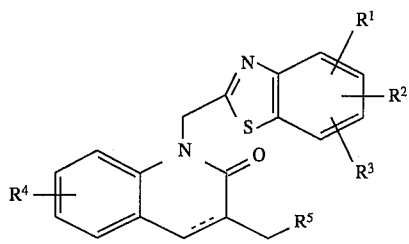

wherein $R^1$, $R^2$ and $R^3$ are the same or different and each is a hydrogen atom or a halogen atom, $R^4$ is a hydrogen atom, a halogen atom or a substituted or unsubstituted lower alkyl, $R^5$ is carboxyl alkoxycarbonyl or aryloxycarbonyl, benzyloxycarbonyl and the broken line means an optional presence of a double bond, or a pharmaceutically acceptable salt thereof.

2. A quinoline-3-acetic acid derivative of claim 1, wherein at least one of $R^1$, $R^2$ and $R^3$ is a halogen atom, or a pharmaceutically acceptable salt thereof.

3. A quinoline-3-acetic acid derivative of claim 1 or claim 2, wherein the halogen atom is a fluorine atom, a bromine atom or a chlorine atom, or a pharmaceutically acceptable salt thereof.

4. A quinoline-3-acetic acid derivative of claim 2 or claim 3, wherein at least two of $R^1$, $R^2$ and $R^3$ are not hydrogen atoms and are bonded at the 4- and 5- positions, the 5- and 7-positions or the 6- and 7-positions, or a pharmacetuically acceptable salt thereof.

5. A quinoline-3-acetic acid derivative of claim 2 or claim 3, wherein $R^1$, $R^2$ and $R^3$ are not hydrogen atoms and are bonded at the 4-, 5- and 7-positions, or a pharmaceutically acceptable salt thereof.

6. A quinoline-3-acetic acid derivative of any one of claims 1 to 5, wherein $R^4$ is bonded at the 6-position, or a pharmaceutically acceptable salt thereof.

7. A quinoline-3-acetic acid derivative of any one of claims 1 to 6, wherein $R^4$ is a lower alkyl, or a pharmaceutically acceptable salt thereof.

8. A quinoline-3-acetic acid derivative of any one of claims 1 to 7, wherein $R^5$ is a carboxyl, a methoxycarbonyl or ethoxycarbonyl, or a pharmaceutically acceptable salt thereof.

9. A quinoline-3-acetic acid derivative of claim 1, which is selected from the group consisting of:

ethyl 1-(4,5,7-trifluorobenzothiazol-2-yl)methyl-2-oxo-1, 2,3,4-tetrahydro- 1H-quinolin-3-ylacetate, ethyl 1-(4,5-difluorobenzothiazol-2-yl)methyl-2-oxo-1,2, 3,4-tetrahydro- 1H-quinolin-3-ylacetate, ethyl 1-(5,7-difluorobenzothiazol-2-yl)methyl-2-oxo-1,2, 3,4-tetrahydro- 1H-quinolin-3-ylacetate, ethyl 1-(6,7-difluorobenzothiazol-2-yl)methyl-2-oxo-1,2, 3,4-tetrahydro- 1H-quinolin-3-ylacetate, ethyl 1-(5-fluorobenzothiazol-2-yl)methyl-2-oxo-1,2,3,4-tetrahydro- 1H-quinolin-3-ylacetate, ethyl 1-(5,7-dichlorobenzothiazol-2-yl)methyl-2-oxo-1,2, 3,4-tetrahydro- 1H-quinolin-3-ylacetate, ethyl 6-methyl-1-(4,5,7-trifluorobenzothiazol-2-yl)methyl-2-oxo- 1,2,3,4-tetrahydro-1H-quinolin-3-ylacetate, ethyl 6-methyl-1-(4,5-difluorobenzothiazol-2-yl)methyl-2-oxo- 1,2,3,4-tetrahydro-1H-quinolin-3-ylacetate, ethyl 6-fluoro-1-(4,5,7-trifluorobenzothiazol-2-yl)methyl-2-oxo- 1,2,3,4- tetrahydro-1H-quinolin-3-ylacetate, ethyl 1-(4,5,7-trifluorobenzothiazol-2-yl)methyl-2-oxo-1, 2,-dihydro- 1H-quinolin-3-ylacetate, 1-(4,5,7-trifluorobenzothiazol-2-yl)methyl-2-oxo-1,2,3,4-tetrahydro-1H-quinolin-3-ylacetic acid, 1-(4,5-difluorobenzothiazol-2-yl)methyl-2-oxo-1,2,3,4-tetrahydro-1H-quinolin-3-ylacetic acid, 1-(5,7-difluorobenzothiazol-2-yl)methyl-2-oxo-1,2,3,4-tetrahydro-1H-quinolin-3-ylacetic acid, 1-(6,7-difluorobenzothiazol-2-yl)methyl-2-oxo-1,2,3,4-tetrahydro-1H-quinolin-3-ylacetic acid, 1-(5-fluorobenzothiazol-2-yl)methyl-2-oxo-1,2,3,4-tetrahydro-1H-quinolin-3-ylacetic acid, 1-(5,7-dichlorobenzothiazol-2-yl)methyl-2-oxo-1,2,3,4-tetrahydro-1H-quinolin-3-ylacetic acid, 6-methyl-1-(4,5,7-trifluorobenzothiazol-2-yl)methyl-2-oxo-1,2,3,4-tetrahydro-1H-quinolin-3-ylacetic acid, 6-methyl-1-(4,5-difluorobenzothiazol-2-yl)methyl-2-oxo-1,2,3,4-tetrahydro-1H-quinolin-3-ylacetic acid, 6-fluoro-1-(4,5,7-trifluorobenzothiazol-2-yl)methyl-2-oxo-1,2,3,4-tetrahydro-1H-quinolin-3-ylacetic acid and 1-(4,5,7-trifluorobenzothiazol-2-yl)methyl-2-oxo-1,2-dihydro-1H-quinolin-3-ylacetic acid, or a pharmaceutically acceptable salt thereof.

10. A pharmaceutical composition comprising the quinoline-3-acetic acid derivative of any one of claims 1 to 9 or a pharmaceutically acceptable salt thereof and a pharmaceutically acceptable diluent.

11. The pharmaceutical composition of claim 10, which is an aldose reductase inhibitor.

12. A method for inhibiting aldose reductase, in a mammal, comprising administering to a mammal an amount effective for inhibiting aldose reductase of the quinoline-3-acetic acid derivative of any one of claims 1 to 9 or a pharmaceutically acceptable salt thereof.

13. A method for preventing and/or treating in a mammal a complication of diabetes selected from the group consisting of faulty union of corneal injury, diabetic neurosis, nephropatby, retinopathy and cataract, comprising administering to a mammal an amount effective to prevent and/or treat said complication of the quinoline-3-acetic acid derivative of any one of claims 1 to 9 or a pharmaceutically acceptable salt thereof.

* * * * *